(12) United States Patent
Saxena

(10) Patent No.: US 7,229,824 B2
(45) Date of Patent: Jun. 12, 2007

(54) RIBONUCLEASES AND METHODS OF MAKING THEM RECOMBINANTLY

(75) Inventor: Shailendra K. Saxena, West Orange, NJ (US)

(73) Assignee: Alfacell Corporation, Bloomfield, NJ (US)

( * ) Notice: Subject to any disclaimer, the term of this patent is extended or adjusted under 35 U.S.C. 154(b) by 312 days.

(21) Appl. No.: 10/621,741

(22) Filed: Jul. 17, 2003

(65) Prior Publication Data

US 2005/0014161 A1    Jan. 20, 2005

(51) Int. Cl.
*C12N 15/00* (2006.01)
*C12N 9/16* (2006.01)
*C12N 1/20* (2006.01)
*C12N 5/06* (2006.01)
*C12P 21/06* (2006.01)
*C07H 21/04* (2006.01)
*C07K 14/00* (2006.01)

(52) U.S. Cl. ............... 435/320.1; 435/252.3; 435/325; 435/196; 435/69.1; 536/23.2; 536/23.1; 530/350

(58) Field of Classification Search ............. 435/320.1, 435/69.1, 325, 252.3, 196; 536/23.1, 23.2, 536/350
See application file for complete search history.

(56) References Cited

U.S. PATENT DOCUMENTS 6,239,257 B1 * 5/2001 Ardelt .................. 530/350

OTHER PUBLICATIONS

Lehninger, A.L. (1975) Biochemistry, Second Edition, p. 962.*
Studier, F.W., et al. (1990) Met. Enzym. 185, 60-89.*
Huang, H-C, et al. (1998) J. Biol. Chem. 273(11), 6395-6401.*
Guerro, S.A., et al. (2000) Appl. Microbiol. Biotechnol. 53, 410-414.*

* cited by examiner

Primary Examiner—Delia M. Ramirez

(57) ABSTRACT

Methods for recombinantly producing new RNases, as well as previously-known RNases, are disclosed. The new RNases are active against human carcinoma cells.

3 Claims, 7 Drawing Sheets

RIBONUCLEASES AND METHODS OF MAKING THEM RECOMBINANTLY

BACKGROUND OF THE INVENTION

The invention relates to pharmaceuticals, and more particularly relates to pharmaceuticals for treating tumors in humans. In its most immediate sense, the invention relates to bioactive ribonucleases ("RNases").

Some RNases are known to be active against certain human tumor cells. For example, commonly-owned U.S. Pat. No. 5,559,212 discloses and claims ranpirnase, an RNase pharmaceutical that is presently known by the registered trademark ONCONASE and that is presently the subject of Phase III clinical trials. And, commonly-owned U.S. Pat. No. 6,239,257 B1 discloses four RNase proteins that belong to the pancreatic RNase A superfamily, each possessing activity against two human carcinoma cell lines.

Attention is now being directed to "targeting" pharmaceuticals to deliver them to particular cell receptors of interest. This is accomplished by selecting a targeting moiety that is preferentially attracted to the desired cell receptor and attaching (as by conjugation or fusion) the targeting moiety to the pharmaceutical.

Commonly-owned patent No. U.S. Pat. No. 6,175,003 B1 discusses the concept of targeting therapeutically active RNases by "cysteinizing" them. In the case of ranpirnase, this can be accomplished by conjugating the targeting moiety to the cysteine residue at position 72. While this approach is promising and is still under investigation, some people believe that it may be difficult to obtain regulatory approval for a conjugate and that a fusion protein would have an easier path to regulatory approval.

The N-terminal residue of ranpirnase is pyroglutamic acid. This "blocks" the N-terminal, i.e. makes it impossible to attach other amino acid residues to the left of the N-terminal. For this reason, it is not possible to create a fusion protein by attaching a targeting moiety to the N-terminal of ranpirnase. And, while it is possible to remove the pyroglutamic acid residue and to attach a targeting moiety to the aspartic amino acid residue in the second position of ranpirnase, removal of the pyroglutamic acid residue eliminates the bioactivity of ranpirnase.

However, the RNases disclosed in the above-referenced patent No. U.S. Pat. No. 6,239,257 B1 are not only active against certain human cancer cells, but also lack "blocked" N-terminals. For this reason, each of these RNases could be used to make a targeted fusion protein by attaching a targeting moiety to its N-terminal end.

It would be advantageous to provide methods for manufacturing such proteins recombinantly.

It would further be advantageous to provide bioactive proteins that could be made into targeted fusion proteins.

In accordance with one aspect of the invention, methods are provided for recombinantly manufacturing the proteins disclosed in patent No. U.S. Pat. No. 6,239,257 B1.

In accordance with another aspect of the invention, new proteins are provided that possess activity against human carcinoma cells and that can also be manufactured recombinantly. One of the proteins is "cysteinized" to permit easier conjugation to a targeting moiety.

When recombinantly manufactured, one of the proteins disclosed in patent No. U.S. Pat. No. 6,239,257 B1 retains its activity against human carcinoma cells even when a number of different leader sequences are attached to its N-terminal. The leader sequences form parts of the vector in which the DNA of the protein of interest has been inserted.

As will be seen below, there is a compelling body of evidence that such leader sequences do not, when attached to the N-terminal of any one of the family of RNase proteins disclosed in U.S. Pat. No. 6,239,257 B1, affect the bioactivity of the protein.

BRIEF DESCRIPTION OF THE DRAWINGS

The invention will be better understood with reference to the following exemplary and non-limiting drawings, in which.

DETAILED DESCRIPTION OF PREFERRED EMBODIMENTS

Figure 1:
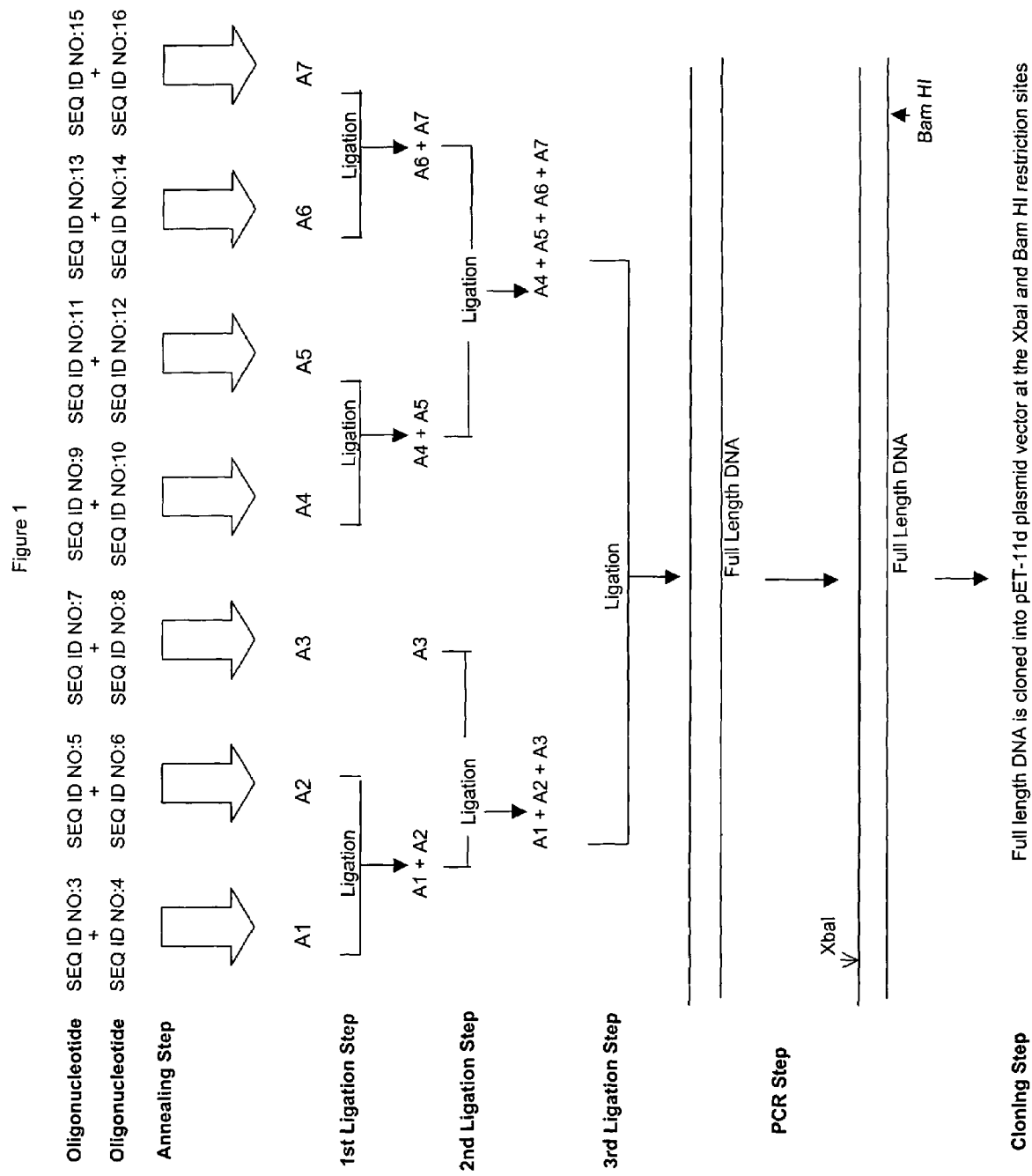
FIG. 1 is a flow chart illustrating the process for recombinantly manufacturing the protein identified as 2325p4 in U.S. Pat. No. 6,239,257 B1.

A common procedure is used in the following Examples 1, 2, and 3, which relate to recombinant production of proteins identified as 2325p4, 2325p6, and 2728 in U.S. Pat. No. 6,239,257 B1. This procedure will be described first at a general level and then in more detail. Thereafter, each Example will be given.

At a general level, fourteen oligonucleotides for each gene (seven representing the top DNA strand and seven for the bottom DNA strand) were synthesized. The oligonucleotides were cautiously designed so that:

a) after annealing, complementary oligonucleotides had an overhang at the 5' end of each pair, each such overhang being 7 oligonucleotides long; and b) each such overhang had at least three nucleotide mismatches with the overhang of an unfitting pair of oligonucleotides.

Seven pairs of oligonucleotides, representing both strands of the full-length gene, were obtained after annealing. The duplex oligonucleotides were ligated in three steps to form full-length DNA of the protein of interest. This full-length DNA was then subjected to PCR. The PCR primers were chosen to:

a) incorporate a XbaI restriction site at the 5' end of the gene and a BamHI restriction site at the 3' end of the gene. These sites were selected so the DNA could be cloned into a pET-11d plasmid vector at these sites.

b) include a translation initiation codon immediately before the first nucleotide of the gene.

c) incorporate a translation termination codon immediately after the last nucleotide of the final codon of the gene.

The purified gene thus produced was inserted into a pET11d plasmid vector between XbaI and BamHI restriction sites. The insert positive clones were identified and used to express recombinant protein.

In each instance, the expressed protein had an additional methionine residue at position −1. This was cleaved in vitro using *Aeromonas* aminopeptidase to yield the desired protein.

More specifically, in each instance fourteen oligonucleotides were synthesized and gel purified by Genosys Biotechnologies, Inc. (The Woodlands, Tex.). Each oligonucleotide was phosphorylated at its 5' end using T4 polynucleotide kinase enzyme and its reaction buffer from New England Biolabs, Inc. (Beverly, Mass.). The desired DNA was extracted with Phenol:Chloroform solution (Eastman Kodak Company, Rochester, N.Y.) and unincorporated rATP was removed by ethanol precipitation.

Each solution of complementary oligonucleotides (20 µg each, for a total of 40 µg) was mixed and annealed to form duplex oligonucleotides. Annealing was carried out by placing a tube containing the complementary oligonucleotides in a beaker containing boiling water and then transferring the beaker to a cold room for approximately 18 hours with gentle stirring.

The annealed duplex oligonucleotides were then agarose gel purified using a Jetsorb DNA extraction kit from Genomed Inc. (Research Triangle Park, North Carolina). The duplex oligonucleotides (approximately 10 µg each) were mixed and ligated together in three separate ligation steps at 16° C. for 18 hours using T4 DNA ligase enzyme from New England Biolabs, Inc. (Beverly, Mass.). As above, the DNA in each ligation reaction mixture was precipitated with ethanol after extracting it with Phenol:Chloroform solution. This produced full-length double stranded DNA of the protein of interest.

This product, which was the desired gene, was amplified using PCR and purified from agarose gel using a Jetsorb DNA extraction kit. The purified gene was then digested with XbaI and BamHI restriction enzymes followed by its ligation into a pET11d plasmid vector (Novagen) that had also been digested with XbaI and BamHI restriction enzyme from Stratagene (La Jolla, Calif.). (It will be understood that the use of a pET11d vector, and of XbaI and BamHI restriction sites, is only preferred and not necessary. Another vector, and other restriction sites, could be used instead.)

Then, the ligated reaction mixture was used to transform *E. coli* strain XL1-Blue (Stratagene) competent cells. The clones were identified for the insert DNA of the desired protein in the plasmid DNA preparations by restriction enzyme analysis. The recombinant plasmid DNA was then used as described below to transform the expression host to express the target gene.

*E. coli* BL21(DE3) competent cells (Novagen, Madison, Wis.) were used as an expression host and transformed with the plasmid DNA. (Another expression host could have been used instead.) The recombinant protein was expressed by induction with IPTG. Most of the expressed protein was found in the inclusion bodies and some was also present in the soluble fraction.

To purify the recombinant protein, the bacterial pellet containing the inclusion bodies was resuspended, sonicated and centrifuged using the procedure of Schultz and Baldwin (Protein Science 1, 910–916, 1992), modified as discussed below. The inclusion bodies were washed with 50 mM Tris-HCl buffer, pH 8.5 containing 300 mM sodium chloride and centrifuged. The proteins present in the pellet were then denatured with 6 M guanidine-HCl in 100 mM Tricine buffer, pH 8.5. Thereafter, the proteins were reduced and fully unfolded by adding 0.1 M reduced glutathione followed by incubation at room temperature under nitrogen for 3 h. Then, the proteins were refolded by 10 times dilution with nanopure water followed by incubation at 4–5° C. for 18 h. The refolded protein was then purified by cation exchange chromatography on SP-Sepharose. The SP-Sepharose column was eluted with a linear sodium chloride gradient (0–0.3 M) in 0.15 M sodium acetate buffer, pH 5.0. Finally, the homogeneity of the purified proteins was checked by 10–20% SDS-polyacrylamide gel electrophoresis. Although these steps were preferred to increase the yield of the desired protein, they are not necessary to the invention and may be omitted.

Finally, as stated above, the initial methionine residue at position −1 was cleaved in vitro by *Aeromonas* aminopeptidase. This produced the desired protein.

EXAMPLE 1

Synthesis, Cloning, and Expression of pET11d-2325p4 Plasmid DNA

Example 1 relates to a protein identified as 2325p4 in U.S. Pat. No. 6,239,257 B1, which has the amino acid sequence of SEQ ID NO:1 and the nucleotide sequence of SEQ ID NO:2.

In an initial step, oligonucleotides SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, and SEQ ID NO:16 were synthesized and purified as discussed above.

In the next step (shown at the top of FIG. 1 and described in detail above), pairs of oligonucleotides were mixed and annealed to form duplex oligonucleotides A1, A2, A3, A4, A5, A6, and A7.

These annealed oligonucleotides A1, A2, A3, A4, A5, A6, and A7 were then agarose gel purified as discussed above. The annealed and purified oligonucleotides were then mixed and ligated together in three separate ligation steps shown in the center of FIG. 1 using the procedure described above. This produced full-length DNA.

1 µg of the full-length DNA was subjected to PCR with primers SEQ ID NO:3 and SEQ ID NO:16. As discussed above, the primers provide XbaI and BamHI restriction sites permitting the gene to be inserted in a pET11d vector.

The gene of the 2325p4 protein was agarose gel purified as discussed above. The purified 2325p4 gene was then digested with XbaI and BamHI restriction enzyme and ligated into a pET11d plasmid vector as discussed above.

Then, as discussed above, the ligated reaction mixture was used to transform *E. coli* XL1-Blue competent cells, and the recombinant plasmid pET11d-2325p4 DNA was then used to transform the expression host to express the target gene as discussed above.

The expressed protein has the amino acid sequence shown in SEQ ID NO:59, in which an additional N-terminal methionine residue is followed by lysine, the first amino acid of the 2325p4 protein. The N-terminal additional methionine residue was cleaved as stated above_to yield 2325p4 recombinant protein having the amino acid sequence SEQ ID NO:1.

As stated in U.S. Pat. No. 6,239,257 B1, 2325p4 protein inhibited growth of human submaxillary gland carcinoma (A-253) cells and human bladder carcinoma (T-24) cells.

EXAMPLE 2

Synthesis, Cloning, and Expression of pET11d-2325p6 Plasmid DNA

Example 2 relates to a protein identified as 2325p6 in U.S. Pat. No. 6,239,257 B1, which has the amino acid sequence of SEQ ID NO:17 and the nucleotide sequence of SEQ ID NO:18.

In an initial step, oligonucleotides SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, and SEQ ID NO:32 were synthesized and purified as discussed above.

Figure 2:
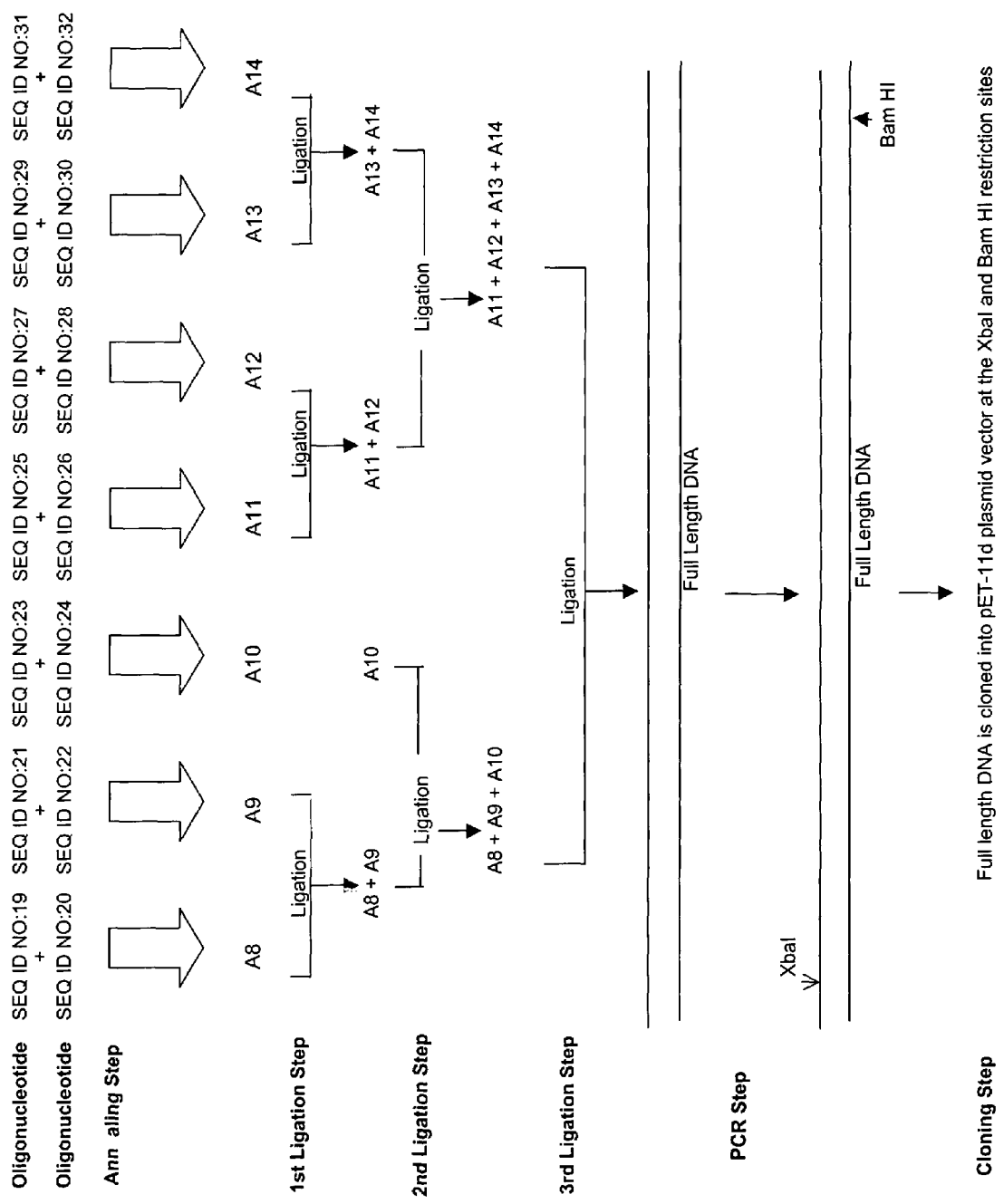
FIG. 2 is a flow chart illustrating the process for recombinantly manufacturing the protein identified as 2325p6 in U.S. Pat. No. 6,239,257 B1.

In the next step (shown at the top of FIG. 2 and described in detail above), pairs of oligonucleotides were mixed and annealed to form duplex oligonucleotides A8, A9, A10, A11, A12, A13, and A14.

These annealed oligonucleotides A8, A9, A10, A11, A12, A13, and A14 were agarose gel purified as discussed above. The annealed oligonucleotides were mixed and ligated together in three separate ligation steps shown in the center of FIG. 2 using the procedure described above. This produced full-length DNA.

1 µg of the full-length DNA was subjected to PCR with primers SEQ ID NO:32 and SEQ ID NO:33. As discussed above, the primers provide XbaI and BamHI restriction sites permitting the gene to be inserted into a pET11d plasmid vector.

The double stranded full-length PCR product, namely the gene of the 2325p6 protein, was purified from agarose gel and ligated into a pET-11d plasmid vector at XbaI and BamHI restriction site, all using the procedure discussed above.

Then, using the same procedure described above, E. coli XL1-Blue competent cells were transformed and the recombinant plasmid pET11d-2325p6 DNA was used to transform the expression host (E. coli BL21(DE3) competent cells) to express the target gene.

The expressed protein has the amino acid sequence shown in SEQ ID NO:60, in which an additional N-terminal methionine amino acid is followed by lysine, the first amino acid of the 2325p6 protein. The N-terminal additional methionine residue was cleaved as stated above to yield 2325p6 recombinant protein having the amino acid sequence SEQ ID NO: 17.

As stated in U.S. Pat. No. 6,239,257 B1, 2325p6 protein inhibited growth of human submaxillary gland carcinoma (A-253) cells and human bladder carcinoma (T-24) cells.

EXAMPLE 3

Synthesis, Cloning, and Expression of pET11d-2728 Plasmid DNA

Example 3 relates to a protein identified as 2728 in U.S. Pat. No. 6,239,257 B1, which has the amino acid sequence of SEQ ID NO:34 and the nucleotide sequence of SEQ ID NO:35.

In an initial step, oligonucleotides SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, and SEQ ID NO:49 were synthesized and purified as discussed above.

Figure 3:
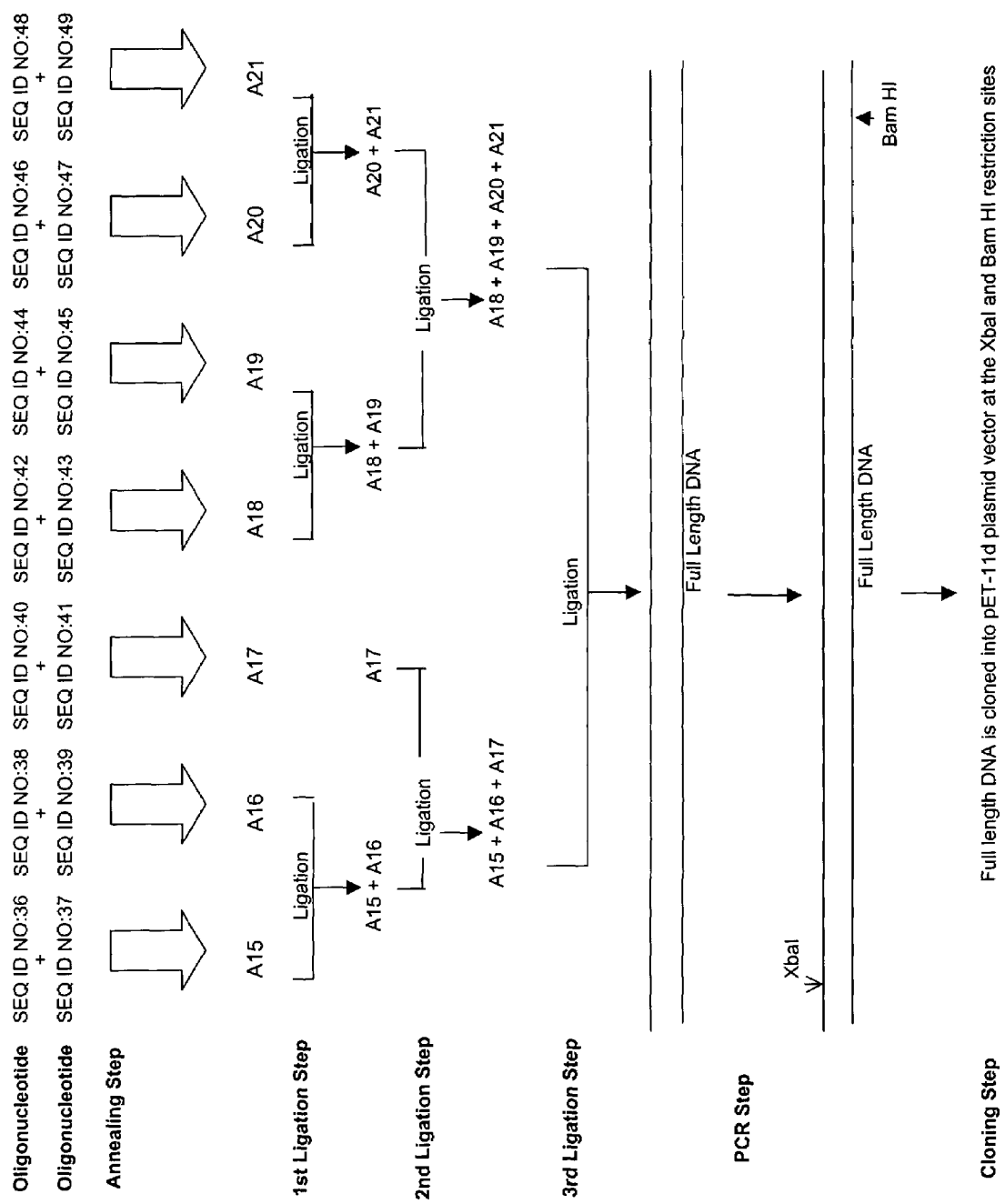
FIG. 3 is a flow chart illustrating the process for recombinantly manufacturing the protein identified as 2728 in U.S. Pat. No. 6,239,257 B1.

In the next step (shown at the top of FIG. 3 and described in detail above), pairs of oligonucleotides were mixed and annealed to form duplex oligonucleotides A15, A16, A17, A18, A19, A20, and A21.

These annealed oligonucleotides A15, A16, A17, A18, A19, A20, and A21 were agarose gel purified as discussed above. The annealed oligonucleotides were mixed and ligated together in three separate ligation steps shown in the center of FIG. 3 using the procedure described above. This produced full-length DNA.

1 µg of the full-length DNA was subjected to PCR with primers SEQ ID NO:33 and SEQ ID NO:49. As discussed above, the primers provide XbaI and BamHI restriction sites permitting the gene to be inserted into a pET11d plasmid vector.

The double stranded full-length PCR product, namely the gene of the 2728 protein, was purified from agarose gel and ligated into a pET11d plasmid vector, all using the procedure described above.

Then, using the same procedure described above, E. coli XL1-Blue competent cells were transformed and the recombinant plasmid DNA pET11d-2728 was used to transform the expression host cell (E. coli BL21(DE3) competent cells) to express the target gene.

The expressed protein has the amino acid sequence shown in SEQ ID NO: 61, in which an additional N-terminal methionine amino acid is followed by lysine, the first amino acid of the 2728 protein. The N-terminal additional methionine residue was cleaved as stated above to yield 2728 recombinant protein having the amino acid sequence SEQ ID NO: 34.

As stated in U.S. Pat. No. 6,239,257 B1, 2728 protein inhibited growth of human submaxillary gland carcinoma (A-253) cells and human bladder carcinoma (T-24) cells.

EXAMPLE 4

Synthesis and Cloning of pET22b-2325p4 DNA

Figure 4:
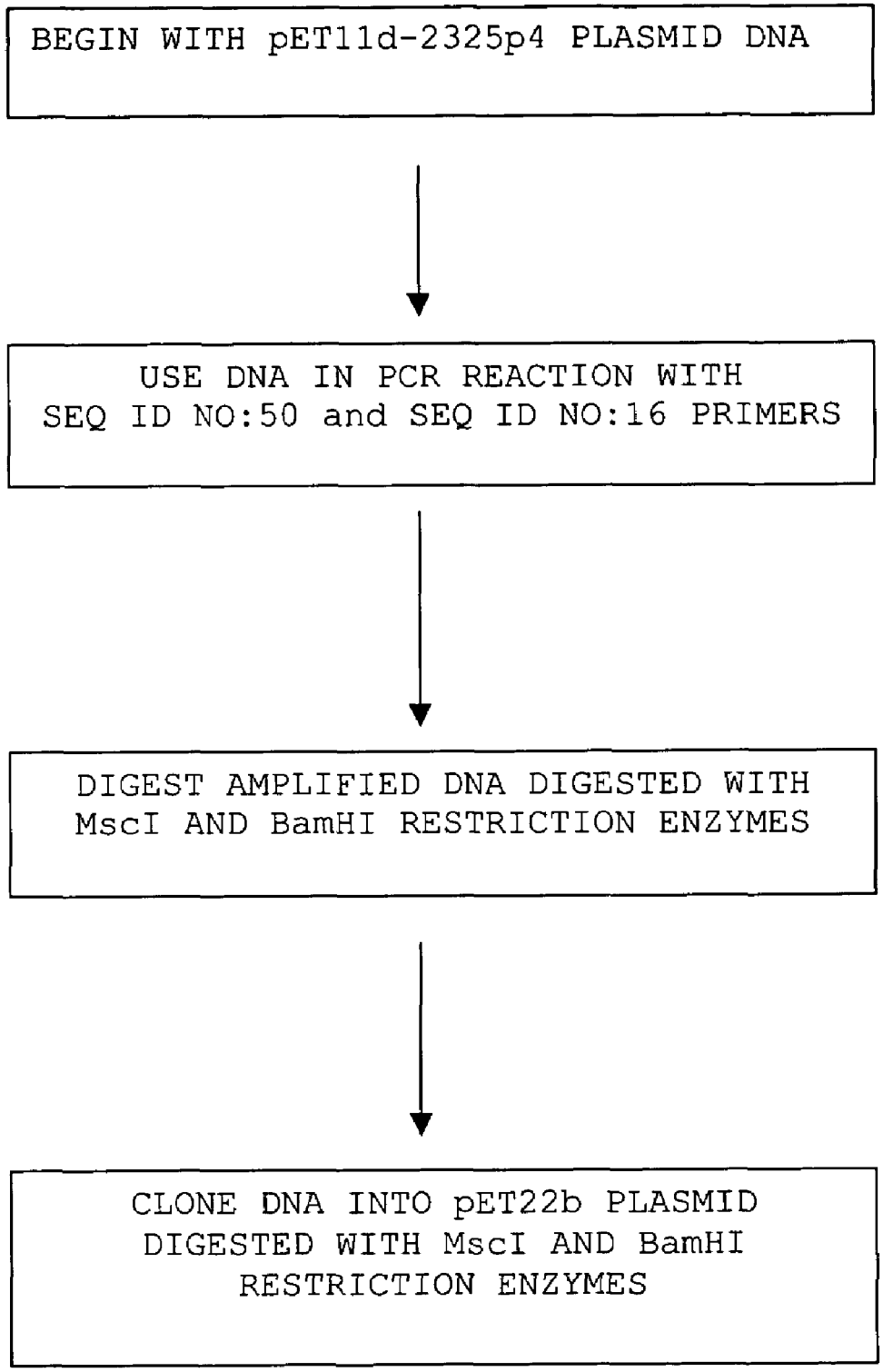
FIG. 4 is a flow chart illustrating the process for manufacturing pET22b-2325p4 DNA.

As stated above, the protein identified as 2325p4 in U.S. Pat. No. 6,239,257 B1 has the amino acid sequence of SEQ ID NO:1 and the nucleotide sequence of SEQ ID NO:2. The process for making pET22b-2325p4 DNA is illustrated in FIG. 4.

The above-described pET11d-2325p4 plasmid DNA (consisting of 2325p4 DNA cloned in a pET-11d vector) was used as a template for amplification using forward and reverse DNA primers in PCR to produce 2325p4 DNA in a form suitable for cloning into a pET22b plasmid between the MscI and BamHI restriction sites.

The forward primer, which is constructed to have SEQ ID NO:50, was designed to incorporate a MscI restriction site at the 5' end of the gene. The reverse primer, which is constructed to have SEQ ID NO:16, was designed to have a stop codon flanked by a BamHI site at the 3' end of the gene. These primers were used in a single step of PCR amplification. The amplified DNA was then digested with MscI and BamHI restriction enzyme and cloned into pET22b plasmid digested with MscI and BamHI restriction enzymes. The newly constructed plasmid was named pET22b-2325p4 DNA.

EXAMPLE 5

Synthesis, Cloning, and Expression of pET11d-2325p4a Plasmid DNA pET11d-2325p4a DNA has been synthesized by replacing the isoleucine residue at position 44 of pET11d-2325p4 DNA with valine using site-directed mutagenesis. 2325p4a protein has the amino acid sequence of SEQ ID NO:51 and the nucleotide sequence of SEQ ID NO:52.

Primers were designed to generate DNA fragments containing a) an XbaI restriction site at the 5' terminus and b) a stop codon flanked by a BamHI site at the 3' terminus, and mismatched primers were synthesized to change the isoleucine residue at position 44 to valine. The full-length gene of 2325p4a was made in two steps of PCR amplifications using a Perkin Elmer DNA thermal cycler, PCR reagents and DNA polymerase.

Figure 5:
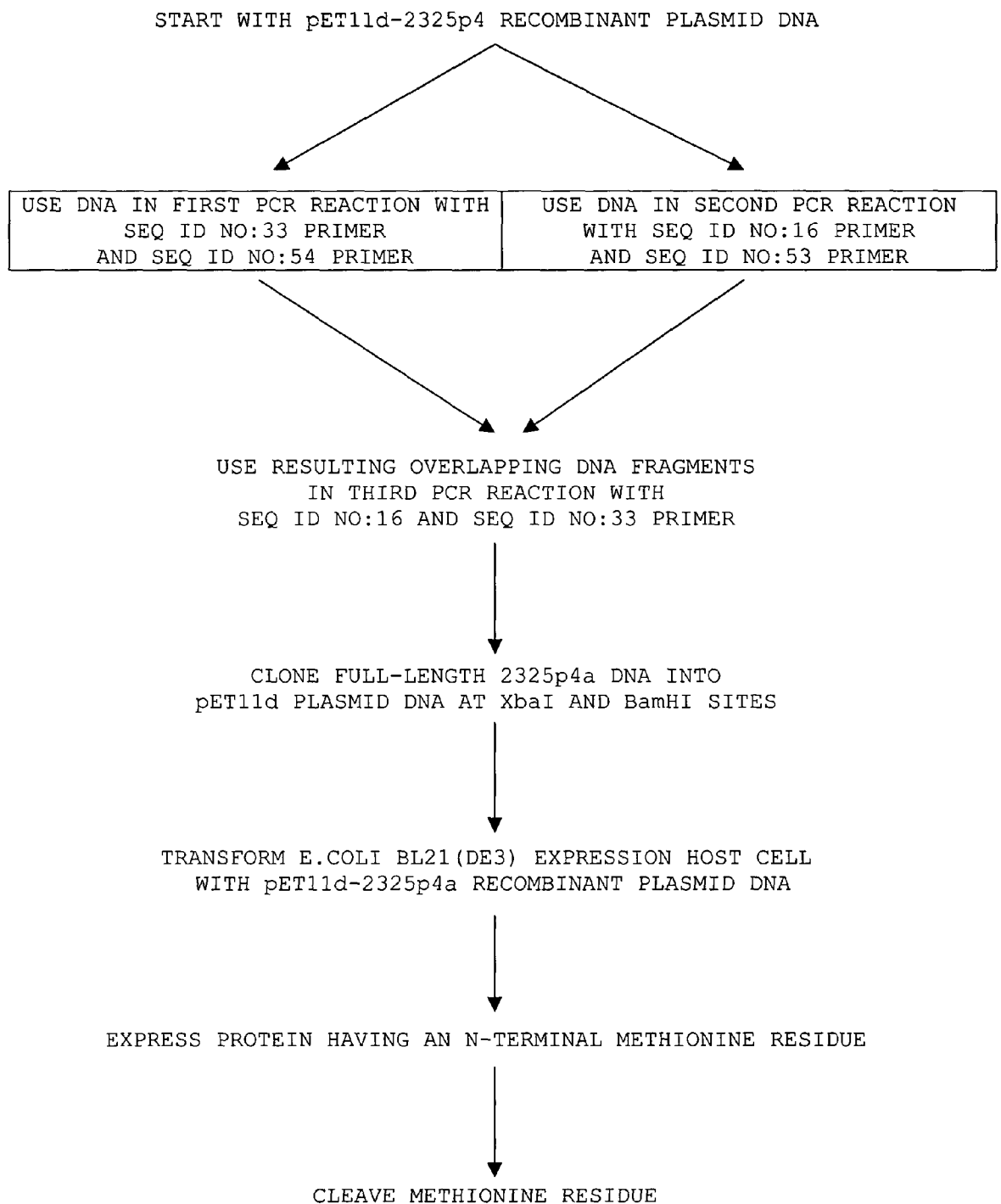
FIG. 5 is a flow chart illustrating the process for recombinantly manufacturing the protein identified as 2325p4a in U.S. Pat. No. 6,239,257 B1.

In the first step of PCR amplification as shown in FIG. 5, two separate PCR reactions were performed using pET11d-2325p4 DNA as a template. In the first PCR reaction, amplification was carried out using primers SEQ ID NO:33 and SEQ ID NO:54 and in the second PCR reaction, amplification was carried out using primers SEQ NO ID:16 and SEQ ID NO:53. These two PCR reactions resulted in two overlapping DNA fragments, both bearing the same mutation in the overlapping region introduced via primer mismatch.

In the second step of PCR amplification, the two overlapping half-fragments were mixed together with primers SEQ ID NO:33 and SEQ ID NO:16 to produce full-length 2325p4a DNA containing the desired mutation. Then, the amplified full-length 2325p4a DNA was gel purified and digested with XbaI and BamHI restriction enzymes and subsequently cloned into pET11d plasmid cut with XbaI and BamHI restriction enzymes. The newly constructed plasmid was named pET11d-2325p4a DNA.

Recombinant 2325p4a protein was expressed and purified using *E. coli* BL21(DE3) competent cells in the same way as described above in Examples 1, 2, and 3. The protein as expressed has the amino acid sequence of SEQ ID NO: 68, with an initial methionine residue that is cleaved in vitro using *Aeromonas* aminopeptidase to yield the protein having the amino acid sequence SEQ ID NO: 51. This protein is active against A-253 cells.

EXAMPLE 6

Synthesis, Cloning, and Expression of pET11d-2325p4-Cys71 DNA

Commonly-owned U.S. Pat. No. 6,175,003 B1 discusses the concept of "cysteinizing" therapeutically active RNases. It would be advantageous to "cysteinize" the 2324p4 protein disclosed in the above-referenced '257 patent to facilitate conjugation of a targeting moiety thereto. The 2325p4 protein has now been cysteinized by replacing the threonine residue at position 71 with cysteine using site-directed mutagenesis to form 2325p4-Cys71, which has the amino acid sequence of SEQ ID NO: 55 and the nucleotide sequence of SEQ ID NO: 56.

Primers were designed to generate DNA fragments containing a) an XbaI restriction site at the 5' terminus and b) a stop codon flanked by a BamHI site at the 3' terminus, and mismatched primers were synthesized to change the threonine residue at position 71 to cysteine. The full-length gene of 2325p4-Cys71 was made in two steps of PCR amplifications using a Perkin Elmer DNA thermal cycler, PCR reagents and DNA polymerase.

Figure 6:
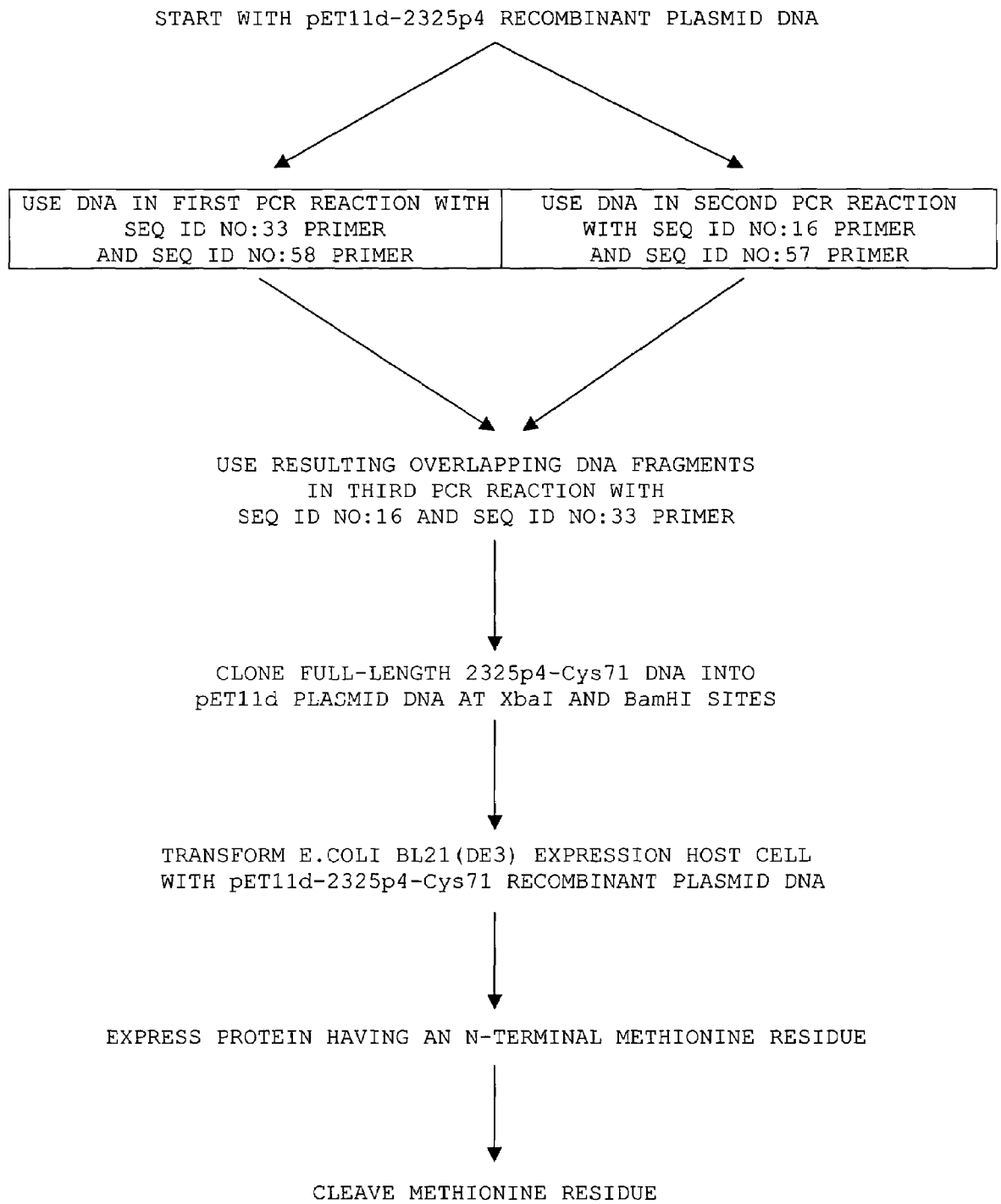
FIG. 6 is a flow chart illustrating the process for recombinantly manufacturing 2325p4-Cys71 protein.

In the first step of PCR amplification as shown in FIG. 6, two separate PCR reactions were performed using pET11d-2325p4 DNA as a template. In the first PCR reaction, amplification was carried out using primers SEQ ID NO:33 and SEQ ID NO:58, and in the second PCR reaction, amplification was carried out using primers SEQ NO ID: 16 and SEQ ID NO:57. These two PCR reactions resulted in two overlapping DNA fragments, both bearing the same mutation in the overlapping region introduced via primer mismatch.

In the second step of PCR amplification, the two overlapping half-fragments were mixed together with primers SEQ ID NO:33 and SEQ ID NO:16 to produce full-length 2325p4-Cys71 DNA containing the desired mutation. Then, the amplified full-length 2325p4-Cys71 DNA was gel purified and digested with XbaI and BamHI restriction enzymes and subsequently cloned into pET-11d plasmid cut with XbaI and BamHI restriction enzymes. The newly constructed plasmid was named pET11d-2325p4-Cys71 DNA.

Recombinant 2325p4-Cys71 protein was expressed and purified using *E. coli* BL21(DE3) competent cells in the same way as described above in Examples 1, 2, and 3. The protein as expressed has the amino acid sequence of SEQ ID NO: 69, with an initial methionine residue that is cleaved in vitro using *Aeromonas* aminopeptidase to yield the protein having the amino acid sequence SEQ ID NO: 55. This protein is active against A-253 cells.

Quite obviously, a targeting moiety can be conjugated to the cysteine residue at position 71 of the 2325p4-Cys71 protein to direct it to a particular cell receptor of interest. The selection of an appropriate moiety is within the skill of a person skilled in the art.

EXAMPLE 7

Synthesis, Cloning, and Expression of pET22b-hEGF-linker-2325p4-Cys71 Plasmid DNA A fusion gene (hEGF-linker-2325p4-Cys71 DNA) cloned in pET22 plasmid vector has been synthesized and expressed. The recombinantly produced hEGF-linker-2325p4-Cys71 fusion protein has the amino acid sequence of SEQ ID NO:70 and the nucleotide sequence of SEQ ID NO:71.

SEQ ID NO:70 is 176 residues long, and consists of:
a) the sequence of hEGF protein (residues 1 to 53);
b) the sequence of the Linker (residues 54 to 62); and
c) the sequence of the 2325p4-Cys71 protein sequence (residues 63 to 176)

Figure 7:
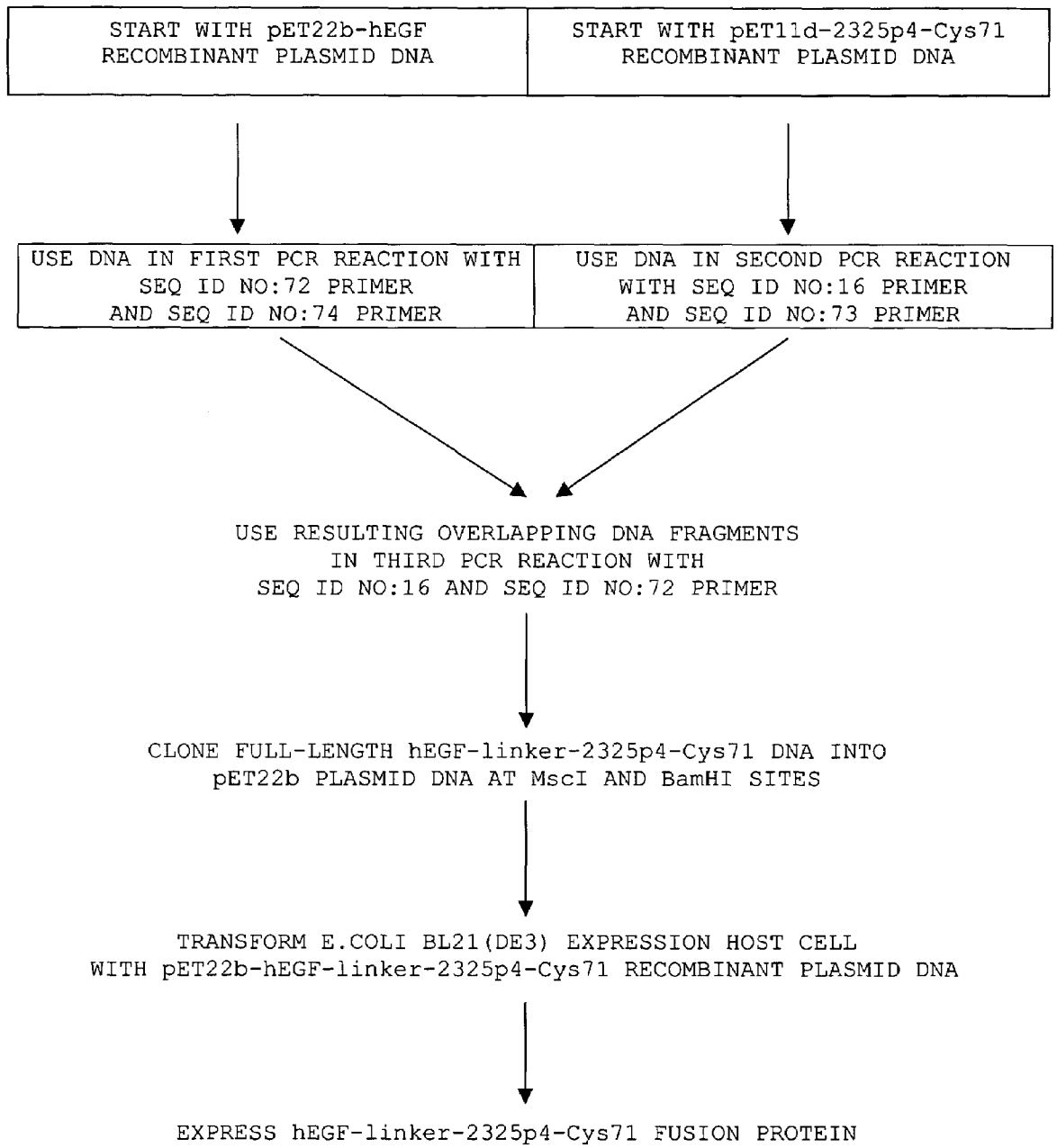
FIG. 7 is a flow chart illustrating the process for manufacturing hEGF-linker-2325p4-Cys71 fusion protein.

The full-length gene of hEGF-linker-2325p4-Cys71 was synthesized as shown in FIG. 7, using three steps of PCR amplification carried out using a Perkin Elmer DNA thermal cycler, PCR reagents, and DNA polymerase. pET22b-hEGF DNA and pET11d-2325p4-Cys71 DNA were used as templates for amplification.

In the first step of PCR amplification, the plasmid pET22b-hEGF DNA was used as a template for amplification using primers SEQ ID NO:72 and SEQ ID NO:74. The primer of SEQ ID NO:74 has the C-terminal nucleotide sequence of hEGF, followed by the nucleotide sequence of the linker.

In the second step of PCR the plasmid pET11d-2325p4-Cys71 DNA was used as a template for amplification using primers SEQ ID NO:16 and SEQ ID NO:73. As stated above, the primer of SEQ ID NO:16 was designed to generate a stop codon flanked by a BamHI site at the 3' terminus. The primer of SEQ ID NO:73 contains the nucleotide sequence of the linker, followed by the N-terminal nucleotide sequence of 2325p4-Cys71 DNA.

These two PCR reactions resulted in two overlapping DNA fragments. In the third PCR step, these two overlapping fragments were mixed together with primer SEQ ID NO:72 and SEQ ID NO:16 to produce full-length hEGF-linker-2325p4-Cys71 DNA. The amplified full-length hEGF-linker-2325p4-Cys71 DNA was agarose gel purified as above, digested with BamHI restriction enzyme, and finally ligated into pET22b plasmid cut with MscI and BamHI restriction enzymes.

The newly constructed plasmid was named pET22b-hEGF-linker-2325p4-Cys71 DNA.

*E. coli* BL21(DE3) competent cells were transformed with pET22b-hEGF-linker-2325p4-Cys71 plasmid DNA and the recombinant protein was expressed and as in Examples 1, 2, and 3 above. The protein as expressed has the amino acid sequence of SEQ ID NO: 70. This protein is active against A-253 cells.

EXAMPLE 8

Expression of Proteins from pET22b-2325p4 Plasmid

A surprising result occurred when the 2325p4 protein was expressed in *E. coli* BL21(DE3) competent cells from pET22b-2325p4 plasmid as discussed above in Example 1. Four separate bioactive proteins were expressed, and all of them were active against A-253 cells. The first of these was the 2325p4 protein, which has the amino acid sequence shown in SEQ ID NO:1.

The second protein was the 2325p4 protein preceded by a two residue long leader sequence having the amino acid sequence of SEQ ID NO:62 (the second protein therefore has the amino acid sequence of SEQ ID NO:63). The third protein was the 2325p4 protein preceded by a seven residue long leader sequence having the amino acid sequence of SEQ ID NO:64 (the third protein therefore has the amino acid sequence of SEQ ID NO:65). The fourth protein was the 2325p4 protein preceded by a twenty-two residue long leader sequence having the amino acid sequence of SEQ ID NO:66 (the fourth protein therefore has the amino acid sequence of SEQ ID NO: 67). Each of these leader sequences is derived from the pelB leader sequence of the pET22b vector.

To a person skilled in the art, the fact that all four of these proteins remained active is very strong evidence that any protein made up of the 2325p4 protein preceded by at least one and at most all of the residues in the seven residue long leader sequence of SEQ ID NO:64 in order will be active as well. And, the same is true of any protein made up of the 2325p4 protein preceded by at least one and at most all of the residues in the twenty two residue long leader sequence of SEQ ID NO:66 in order. In other words, since the leader sequences of SEQ ID NO:64 and SEQ ID NO:66 did not affect the activity of the 2325p4 protein, any person ordinarily skilled in the art would expect that shortened versions of these leader sequences would, when likewise attached at the N-terminal end of the 2325p4 protein, leave the bioactivity of the 2325p4 protein unaffected.

Furthermore, given that the 2325p6 and 2728 proteins are also active against A-253 and T-24 cells, a person skilled in the art would conclude that adding all or any similarly-shortened shortened part of the SEQ ID NO:64 or the SEQ ID NO:66 leader sequences to the N-terminal end of the 2325p4 protein, to the N-terminal end of the 2325p6 protein, or to the N-terminal end of the 2728 protein, would also produce a bioactive protein. This is because these proteins are highly homologous and have highly similar activities against the same cancer cells.

Although one or more preferred embodiments have been described above, the invention is defined only by the following claims.

The invention claimed is:

1. A vector containing the DNA of SEQ ID NO: 2 encoding the ribonuclease of SEQ ID NO: 1.

2. A pET11d plasmid vector containing the DNA of SEQ ID NO: 2 encoding the ribonuclease of SEQ ID NO: 1.

3. A pET22b plasmid vector containing the DNA of SEQ ID NO: 2 encoding the ribonuclease of SEQ ID NO: 1.

* * * * *

SEQUENCE LISTING

```
<160> NUMBER OF SEQ ID NOS: 74

<210> SEQ ID NO 1
<211> LENGTH: 114
<212> TYPE: PRT
<213> ORGANISM: Rana pipiens

<400> SEQUENCE: 1

Lys Pro Lys Glu Asp Arg Glu Trp Glu Lys Phe Lys Thr Lys His Ile
1               5                   10                  15

Thr Ser Gln Ser Val Ala Asp Phe Asn Cys Asn Arg Thr Met Asn Asp
            20                  25                  30

Pro Ala Tyr Thr Pro Asp Gly Gln Cys Lys Pro Ile Asn Thr Phe Ile
        35                  40                  45

His Ser Thr Thr Gly Pro Val Lys Glu Ile Cys Arg Arg Ala Thr Gly
    50                  55                  60

Arg Val Asn Lys Ser Ser Thr Gln Gln Phe Thr Leu Thr Thr Cys Lys
65                  70                  75                  80

Asn Pro Ile Arg Cys Lys Tyr Ser Gln Ser Asn Thr Thr Asn Phe Ile
                85                  90                  95
```

Cys Ile Thr Cys Arg Asp Asn Tyr Pro Val His Phe Val Lys Thr Gly
            100                 105                 110

Lys Cys

<210> SEQ ID NO 2
<211> LENGTH: 342
<212> TYPE: DNA
<213> ORGANISM: Rana pipiens

<400> SEQUENCE: 2
aaaccgaaag aagaccgtga atgggaaaaa ttcaaaacta acatatcac ttctcagtct      60 gttgctgact caactgcaa ccgtactatg aacgacccgg cttacactcc ggacggtcag    120
tgcaaaccga tcaacacttt catccattct actactggtc cggttaaaga atctgccgt    180 cgtgctactg gtcgtgttaa caaatcttct actcagcagt tcactctgac tacttgcaaa    240
aacccgatcc gttgcaaata ctctcagtct aacactacta acttcatctg catcacttgc    300
cgtgacaact acccggttca tttcgttaaa actggtaaat gc                       342

<210> SEQ ID NO 3
<211> LENGTH: 56
<212> TYPE: DNA
<213> ORGANISM: Artificial
<220> FEATURE:
<223> OTHER INFORMATION: Artificially synthesized sequence

<400> SEQUENCE: 3
taattttgtt taactttaag aaggagatat accatgaaac cgaaagaaga ccgtga        56

<210> SEQ ID NO 4
<211> LENGTH: 63
<212> TYPE: DNA
<213> ORGANISM: Artificial
<220> FEATURE:
<223> OTHER INFORMATION: Artificially synthesized sequence complimentary
      to SEQ ID NO:3

<400> SEQUENCE: 4
ttcccattca cggtcttctt tcggtttcat ggtatatctc cttcttaaag ttaaacaaaa    60
tta                                                                  63

<210> SEQ ID NO 5
<211> LENGTH: 57
<212> TYPE: DNA
<213> ORGANISM: Artificial
<220> FEATURE:
<223> OTHER INFORMATION: Artificially synthesized sequence

<400> SEQUENCE: 5
atgggaaaaa ttcaaaacta acatatcac ttctcagtct gttgctgact tcaactg        57

<210> SEQ ID NO 6
<211> LENGTH: 57
<212> TYPE: DNA
<213> ORGANISM: Artificial
<220> FEATURE:
<223> OTHER INFORMATION: Artificially synthesized sequence complementary
      to SEQ ID NO:5

<400> SEQUENCE: 6
acggttgcag ttgaagtcag caacagactg agaagtgata tgtttagttt tgaattt        57

<210> SEQ ID NO 7
<211> LENGTH: 60
<212> TYPE: DNA
<213> ORGANISM: Artificial
<220> FEATURE:
<223> OTHER INFORMATION: Artificially synthesized sequence

<400> SEQUENCE: 7
caaccgtact atgaacgacc cggcttacac tccggacggt cagtgcaaac cgatcaacac    60

<210> SEQ ID NO 8
<211> LENGTH: 60
<212> TYPE: DNA
<213> ORGANISM: Artificial
<220> FEATURE:
<223> OTHER INFORMATION: Artificially synthesized sequence complimentary
      to SEQ ID NO:7

<400> SEQUENCE: 8
gatgaaagtg ttgatcggtt tgcactgacc gtccggagtg taagccgggt cgttcatagt    60

<210> SEQ ID NO 9
<211> LENGTH: 52
<212> TYPE: DNA
<213> ORGANISM: Artificial
<220> FEATURE:
<223> OTHER INFORMATION: Artificially synthesized sequence

<400> SEQUENCE: 9
tttcatccat tctactactg gtccggttaa agaaatctgc cgtcgtgcta ct    52

<210> SEQ ID NO 10
<211> LENGTH: 52
<212> TYPE: DNA
<213> ORGANISM: Artificial
<220> FEATURE:
<223> OTHER INFORMATION: Artificially synthesized sequence complimentary
      to SEQ ID NO:9

<400> SEQUENCE: 10
cacgaccagt agcacgacgg cagatttctt taaccggacc agtagtagaa tg    52

<210> SEQ ID NO 11
<211> LENGTH: 54
<212> TYPE: DNA
<213> ORGANISM: Artificial
<220> FEATURE:
<223> OTHER INFORMATION: Artificially synthesized sequence

<400> SEQUENCE: 11
ggtcgtgtta acaaatcttc tactcagcag ttcactctga ctacttgcaa aaac    54

<210> SEQ ID NO 12
<211> LENGTH: 54
<212> TYPE: DNA
<213> ORGANISM: Artificial
<220> FEATURE:
<223> OTHER INFORMATION: Artificially synthesized sequence complimentary
      to SEQ ID NO:11

<400> SEQUENCE: 12
ggatcgggtt tttgcaagta gtcagagtga actgctgagt agaagatttg ttaa    54

<210> SEQ ID NO 13
<211> LENGTH: 57
<212> TYPE: DNA
<213> ORGANISM: Artificial

```
<220> FEATURE:
<223> OTHER INFORMATION: Artificially synthesized sequence

<400> SEQUENCE: 13
ccgatccgtt gcaaatactc tcagtctaac actactaact tcatctgcat cacttgc        57

<210> SEQ ID NO 14
<211> LENGTH: 57
<212> TYPE: DNA
<213> ORGANISM: Artificial
<220> FEATURE:
<223> OTHER INFORMATION: Artificially synthesized sequence complimentary
      to SEQ ID NO:13

<400> SEQUENCE: 14
tgtcacggca agtgatgcag atgaagttag tagtgttaga ctgagagtat ttgcaac        57

<210> SEQ ID NO 15
<211> LENGTH: 60
<212> TYPE: DNA
<213> ORGANISM: Artificial
<220> FEATURE:
<223> OTHER INFORMATION: Artificially synthesized sequence

<400> SEQUENCE: 15
cgtgacaact acccggttca tttcgttaaa actggtaaat gctagtaggg atccgcgcgg     60

<210> SEQ ID NO 16
<211> LENGTH: 53
<212> TYPE: DNA
<213> ORGANISM: Artificial
<220> FEATURE:
<223> OTHER INFORMATION: Artificially synthesized sequence complimentary
      to SEQ ID NO:15

<400> SEQUENCE: 16
ccgcgcggat ccctactagc atttaccagt tttaacgaaa tgaaccgggt agt            53

<210> SEQ ID NO 17
<211> LENGTH: 114
<212> TYPE: PRT
<213> ORGANISM: Rana pipiens

<400> SEQUENCE: 17

Lys Pro Lys Glu Asp Lys Glu Trp Glu Lys Phe Lys Val Lys His Ile
1               5                   10                  15

Thr Ser Gln Ser Val Ala Asp Phe Asn Cys Thr Ser Thr Met Asn Asn
            20                  25                  30

Pro Asp Phe Thr Pro Asp Gly Gln Cys Lys Pro Ile Asn Thr Phe Ile
        35                  40                  45

His Ser Asn Thr Gly Pro Val Lys Glu Ile Cys Arg Arg Ala Ser Gly
    50                  55                  60

Arg Val Asn Lys Ser Ser Thr Gln Gln Phe Pro Leu Thr Thr Cys Lys
65                  70                  75                  80

Asn Pro Lys Arg Cys Lys Tyr Ser Gln Ser Asn Glu Thr Asn Tyr Ile
                85                  90                  95

Cys Ile Thr Cys Arg Asp Asn Tyr Pro Val His Phe Val Lys Ile Gly
            100                 105                 110

Lys Cys

<210> SEQ ID NO 18
<211> LENGTH: 342
```

<212> TYPE: DNA
<213> ORGANISM: Rana pipiens

<400> SEQUENCE: 18
aaaccgaaag aagacaaaga atgggaaaaa ttcaaagtta acatatcac ttctcagtct    60 gttgctgact tcaactgcac ttctactatg aacaacccgg acttcactcc ggacggtcag   120
tgcaaaccga tcaacacttt catccattct aacactggtc cggttaaaga atctgccgt    180 cgtgcttctg gtcgtgttaa caaatcttct actcagcagt tcccgctgac tacttgcaaa   240
aacccgaaac gttgcaaata ctctcagtct aacgaaacta actacatctg catcacttgc   300
cgtgacaact acccggttca tttcgttaaa atcggtaaat gc                      342

<210> SEQ ID NO 19
<211> LENGTH: 56
<212> TYPE: DNA
<213> ORGANISM: Artificial
<220> FEATURE:
<223> OTHER INFORMATION: Artificially synthesized sequence

<400> SEQUENCE: 19
taattttgtt taactttaag aaggagatat accatgaaac cgaaagaaga caaaga       56

<210> SEQ ID NO 20
<211> LENGTH: 63
<212> TYPE: DNA
<213> ORGANISM: Artificial
<220> FEATURE:
<223> OTHER INFORMATION: Artificially synthesized sequence complimentary
      to SEQ ID NO:19

<400> SEQUENCE: 20
ttcccattct ttgtcttctt tcggtttcat ggtatatctc cttcttaaag ttaaacaaaa    60
tta                                                                 63

<210> SEQ ID NO 21
<211> LENGTH: 57
<212> TYPE: DNA
<213> ORGANISM: Artificial
<220> FEATURE:
<223> OTHER INFORMATION: Artificially synthesized sequence

<400> SEQUENCE: 21
atgggaaaaa ttcaaagtta acatatcac ttctcagtct gttgctgact tcaactg       57

<210> SEQ ID NO 22
<211> LENGTH: 57
<212> TYPE: DNA
<213> ORGANISM: Artificial
<220> FEATURE:
<223> OTHER INFORMATION: Artificially synthesized sequence complimentary
      to SEQ ID NO:21

<400> SEQUENCE: 22
agaagtgcag ttgaagtcag caacagactg agaagtgata tgtttaactt tgaattt      57

<210> SEQ ID NO 23
<211> LENGTH: 60
<212> TYPE: DNA
<213> ORGANISM: Artificial
<220> FEATURE:
<223> OTHER INFORMATION: Artificially synthesized sequence

<400> SEQUENCE: 23
cacttctact atgaacaacc cggacttcac tccggacggt cagtgcaaac cgatcaacac        60

<210> SEQ ID NO 24
<211> LENGTH: 60
<212> TYPE: DNA
<213> ORGANISM: Artificial
<220> FEATURE:
<223> OTHER INFORMATION: Artificially synthesized sequence complimentary
      to SEQ ID NO:23

<400> SEQUENCE: 24
gatgaaagtg ttgatcggtt tgcactgacc gtccggagtg aagtccgggt tgttcatagt        60

<210> SEQ ID NO 25
<211> LENGTH: 52
<212> TYPE: DNA
<213> ORGANISM: Artificial
<220> FEATURE:
<223> OTHER INFORMATION: Artificially synthesized sequence

<400> SEQUENCE: 25
tttcatccat tctaacactg gtccggttaa agaaatctgc cgtcgtgctt ct        52

<210> SEQ ID NO 26
<211> LENGTH: 52
<212> TYPE: DNA
<213> ORGANISM: Artificial
<220> FEATURE:
<223> OTHER INFORMATION: Artificially synthesized sequence complimentary
      to SEQ ID NO:25

<400> SEQUENCE: 26
cacgaccaga agcacgacgg cagatttctt taaccggacc agtgttagaa tg        52

<210> SEQ ID NO 27
<211> LENGTH: 54
<212> TYPE: DNA
<213> ORGANISM: Artificial
<220> FEATURE:
<223> OTHER INFORMATION: Artificially synthesized sequence

<400> SEQUENCE: 27
ggtcgtgtta acaaatcttc tactcagcag ttcccgctga ctacttgcaa aaac        54

<210> SEQ ID NO 28
<211> LENGTH: 54
<212> TYPE: DNA
<213> ORGANISM: Artificial
<220> FEATURE:
<223> OTHER INFORMATION: Artificially synthesized sequence compliment to
      SEQ ID NO:27

<400> SEQUENCE: 28
gtttcgggtt tttgcaagta gtcagcggga actgctgagt agaagatttg ttaa        54

<210> SEQ ID NO 29
<211> LENGTH: 57
<212> TYPE: DNA
<213> ORGANISM: Artificial
<220> FEATURE:
<223> OTHER INFORMATION: Artificially synthesized sequence

<400> SEQUENCE: 29
ccgaaacgtt gcaaatactc tcagtctaac gaaactaact acatctgcat cacttgc        57

<210> SEQ ID NO 30

```
<211> LENGTH: 57
<212> TYPE: DNA
<213> ORGANISM: Artificial
<220> FEATURE:
<223> OTHER INFORMATION: Artificially synthesized sequence compliment to
      SEQ ID NO:29

<400> SEQUENCE: 30
tgtcacggca agtgatgcag atgtagttag tttcgttaga ctgagagtat ttgcaac          57

<210> SEQ ID NO 31
<211> LENGTH: 60
<212> TYPE: DNA
<213> ORGANISM: Artificial
<220> FEATURE:
<223> OTHER INFORMATION: Artificially synthesized sequence

<400> SEQUENCE: 31
cgtgacaact acccggttca tttcgttaaa atcggtaaat gctagtaggg atccgcgcgg       60

<210> SEQ ID NO 32
<211> LENGTH: 53
<212> TYPE: DNA
<213> ORGANISM: Artificial
<220> FEATURE:
<223> OTHER INFORMATION: Artificially synthesized sequence complimentary
      to SEQ ID NO:31

<400> SEQUENCE: 32
ccgcgcggat ccctactagc atttaccgat tttaacgaaa tgaaccgggt agt              53

<210> SEQ ID NO 33
<211> LENGTH: 43
<212> TYPE: DNA
<213> ORGANISM: Artificial Sequence
<220> FEATURE:
<223> OTHER INFORMATION: Artificially synthesized sequence

<400> SEQUENCE: 33
caattcccct ctagaaataa ttttgtttaa ctttaagaag gag                         43

<210> SEQ ID NO 34
<211> LENGTH: 114
<212> TYPE: PRT
<213> ORGANISM: Rana pipiens

<400> SEQUENCE: 34

Lys Pro Lys Glu Asp Lys Glu Trp Val Lys Phe Lys Ala Lys His Ile
1               5                   10                  15

Thr Ser Gln Ser Val Ala Asp Phe Asn Cys Asn Lys Thr Met Asn Asp
            20                  25                  30

Pro Asp Phe Thr Pro Asp Gly Gln Cys Lys Pro Val Asn Thr Phe Ile
        35                  40                  45

His Ser Asn Thr Gly Pro Val Lys Asp Ile Cys Arg Arg Ala Ser Gly
    50                  55                  60

Arg Val Asn Lys Ser Ser Thr Gln Gln Phe Pro Leu Thr Thr Cys Asn
65                  70                  75                  80

Lys Pro Ile Arg Cys Lys Tyr Ser Gln Ser Asn Thr Thr Asn Phe Ile
                85                  90                  95

Cys Ile Thr Cys Arg Asp Asn Tyr Pro Val His Phe Val Lys Ile Gly
            100                 105                 110

Lys Cys
```

<210> SEQ ID NO 35
<211> LENGTH: 342
<212> TYPE: DNA
<213> ORGANISM: Rana pipiens

<400> SEQUENCE: 35

| | | | | |
|---|---|---|---|---|
| aaaccgaaag | aagacaaaga | atgggttaaa | ttcaaagcta aacatatcac ttctcagtct | 60 |
| gttgctgact | tcaactgcaa | caaaactatg | aacgacccgg acttcactcc ggacggtcag | 120 |
| tgcaaaccgg | ttaacacttt | catccattct | aacactggtc cggttaaaga catctgccgt | 180 |
| cgtgcttctg | gtcgtgttaa | caaatcttct | actcagcagt tcccgctgac tacttgcaac | 240 |
| aaaccgatcc | gttgcaaata | ctctcagtct | aacactacta acttcatctg catcacttgc | 300 |
| cgtgacaact | acccggttca | tttcgttaaa | atcggtaaat gc | 342 |

<210> SEQ ID NO 36
<211> LENGTH: 56
<212> TYPE: DNA
<213> ORGANISM: Artificial
<220> FEATURE:
<223> OTHER INFORMATION: Artificially synthesized sequence

<400> SEQUENCE: 36
aattttgttt aactttaaga aggagatata catatgaaac cgaaagaaga caaaga    56

<210> SEQ ID NO 37
<211> LENGTH: 56
<212> TYPE: DNA
<213> ORGANISM: Artificial
<220> FEATURE:
<223> OTHER INFORMATION: Artificially synthesized sequence complimentary
      to SEQ ID NO:36

<400> SEQUENCE: 37
aacccattct ttgtcttctt tcggtttcat atgtatatct ccttcttaaa gttaaa    56

<210> SEQ ID NO 38
<211> LENGTH: 56
<212> TYPE: DNA
<213> ORGANISM: Artificial
<220> FEATURE:
<223> OTHER INFORMATION: Artificially synthesized sequence

<400> SEQUENCE: 38
atgggttaaa ttcaaagcta aacatatcac ttctcagtct gttgctgact tcaact    56

<210> SEQ ID NO 39
<211> LENGTH: 56
<212> TYPE: DNA
<213> ORGANISM: Artificial
<220> FEATURE:
<223> OTHER INFORMATION: Artificially synthesized sequence complimentary
      to SEQ ID NO:38

<400> SEQUENCE: 39
ttgttgcagt tgaagtcagc aacagactga gaagtgatat gtttagcttt gaattt    56

<210> SEQ ID NO 40
<211> LENGTH: 59
<212> TYPE: DNA
<213> ORGANISM: Artificial
<220> FEATURE:
<223> OTHER INFORMATION: Artificially synthesized sequence

<400> SEQUENCE: 40
gcaacaaaac tatgaacgac ccggacttca ctccggacgg tcagtgcaaa ccggttaac    59

<210> SEQ ID NO 41
<211> LENGTH: 59
<212> TYPE: DNA
<213> ORGANISM: Artificial
<220> FEATURE:
<223> OTHER INFORMATION: Artificially synthesized sequence complimentary
      to SEQ ID NO:40

<400> SEQUENCE: 41
tgaaagtgtt aaccggtttg cactgaccgt ccggagtgaa gtccgggtcg ttcatagtt    59

<210> SEQ ID NO 42
<211> LENGTH: 54
<212> TYPE: DNA
<213> ORGANISM: Artificial
<220> FEATURE:
<223> OTHER INFORMATION: Artificially synthesized sequence

<400> SEQUENCE: 42
actttcatcc attctaacac tggtccggtt aaagacatct gccgtcgtgc ttct    54

<210> SEQ ID NO 43
<211> LENGTH: 54
<212> TYPE: DNA
<213> ORGANISM: Artificial
<220> FEATURE:
<223> OTHER INFORMATION: Artificially synthesized sequence complimentary
      to SEQ ID NO:42

<400> SEQUENCE: 43
cacgaccaga agcacgacgg cagatgtctt taaccggacc agtgttagaa tgga    54

<210> SEQ ID NO 44
<211> LENGTH: 54
<212> TYPE: DNA
<213> ORGANISM: Artificial
<220> FEATURE:
<223> OTHER INFORMATION: Artificially synthesized sequence

<400> SEQUENCE: 44
ggtcgtgtta acaaatcttc tactcagcag ttcccgctga ctacttgcaa caaa    54

<210> SEQ ID NO 45
<211> LENGTH: 54
<212> TYPE: DNA
<213> ORGANISM: Artificial
<220> FEATURE:
<223> OTHER INFORMATION: Artificially synthesized sequence complimentary
      to SEQ ID NO:44

<400> SEQUENCE: 45
ggatcggttt gttgcaagta gtcagcggga actgctgagt agaagatttg ttaa    54

<210> SEQ ID NO 46
<211> LENGTH: 57
<212> TYPE: DNA
<213> ORGANISM: Artificial
<220> FEATURE:
<223> OTHER INFORMATION: Artificially synthesized sequence

<400> SEQUENCE: 46
ccgatccgtt gcaaatactc tcagtctaac actactaact tcatctgcat cacttgc    57

-continued

```
<210> SEQ ID NO 47
<211> LENGTH: 57
<212> TYPE: DNA
<213> ORGANISM: Artificial
<220> FEATURE:
<223> OTHER INFORMATION: Artificially synthesized sequence complimentary
      to SEQ ID NO:46

<400> SEQUENCE: 47
tgtcacggca agtgatgcag atgaagttag tagtgttaga ctgagagtat ttgcaac        57

<210> SEQ ID NO 48
<211> LENGTH: 54
<212> TYPE: DNA
<213> ORGANISM: Artificial
<220> FEATURE:
<223> OTHER INFORMATION: Artificially synthesized sequence

<400> SEQUENCE: 48
cgtgacaact acccggttca tttcgttaaa atcggtaaat gctagtaggg atcc           54

<210> SEQ ID NO 49
<211> LENGTH: 53
<212> TYPE: DNA
<213> ORGANISM: Artificial
<220> FEATURE:
<223> OTHER INFORMATION: Artificially synthesized sequence complimentary
      to SEQ ID NO:48

<400> SEQUENCE: 49
ccgcgcggat ccctactagc atttaccgat tttaacgaaa tgaaccgggt agt            53

<210> SEQ ID NO 50
<211> LENGTH: 42
<212> TYPE: DNA
<213> ORGANISM: Artificial
<220> FEATURE:
<223> OTHER INFORMATION: Artificially synthesized sequence

<400> SEQUENCE: 50
gcccagccgg cgatggccaa accgaaagaa gaccgtgaat gg                        42

<210> SEQ ID NO 51
<211> LENGTH: 114
<212> TYPE: PRT
<213> ORGANISM: Rana pipiens

<400> SEQUENCE: 51

Lys Pro Lys Glu Asp Arg Glu Trp Glu Lys Phe Lys Thr Lys His Ile
1               5                   10                  15

Thr Ser Gln Ser Val Ala Asp Phe Asn Cys Asn Arg Thr Met Asn Asp
            20                  25                  30

Pro Ala Tyr Thr Pro Asp Gly Gln Cys Lys Pro Val Asn Thr Phe Ile
        35                  40                  45

His Ser Thr Thr Gly Pro Val Lys Glu Ile Cys Arg Arg Ala Thr Gly
    50                  55                  60

Arg Val Asn Lys Ser Ser Thr Gln Gln Phe Thr Leu Thr Thr Cys Lys
65                  70                  75                  80

Asn Pro Ile Arg Cys Lys Tyr Ser Gln Ser Asn Thr Thr Asn Phe Ile
                85                  90                  95

Cys Ile Thr Cys Arg Asp Asn Tyr Pro Val His Phe Val Lys Thr Gly
            100                 105                 110

Lys Cys
```

<210> SEQ ID NO 52
<211> LENGTH: 342
<212> TYPE: DNA
<213> ORGANISM: Rana pipiens

<400> SEQUENCE: 52

```
aaaccgaaag aagaccgtga atgggaaaaa ttcaaaacta acatatcac ttctcagtct      60
gttgctgact tcaactgcaa ccgtactatg aacgacccgg cttacactcc ggacggtcag    120
tgcaaaccgg ttaacacttt catccattct actactggtc cggttaaaga aatctgccgt    180
cgtgctactg gtcgtgttaa caaatcttct actcagcagt tcactctgac tacttgcaaa    240
aacccgatcc gttgcaaata ctctcagtct aacactacta acttcatctg catcacttgc    300
cgtgacaact acccggttca tttcgttaaa actggtaaat gc                       342
```

<210> SEQ ID NO 53
<211> LENGTH: 39
<212> TYPE: DNA
<213> ORGANISM: Artificial
<220> FEATURE:
<223> OTHER INFORMATION: Artificially synthesized sequence

<400> SEQUENCE: 53

```
gacggtcagt gcaaaccggt taacactttc atccattct                            39
```

<210> SEQ ID NO 54
<211> LENGTH: 39
<212> TYPE: DNA
<213> ORGANISM: Artificial
<220> FEATURE:
<223> OTHER INFORMATION: Artificially synthesized sequence complementary
      to SEQ ID NO:53

<400> SEQUENCE: 54

```
agaatggatg aaagtgttaa ccggtttgca ctgaccgtc                            39
```

<210> SEQ ID NO 55
<211> LENGTH: 114
<212> TYPE: PRT
<213> ORGANISM: Rana pipiens

<400> SEQUENCE: 55

```
Lys Pro Lys Glu Asp Arg Glu Trp Glu Lys Phe Lys Thr Lys His Ile
1               5                   10                  15

Thr Ser Gln Ser Val Ala Asp Phe Asn Cys Asn Arg Thr Met Asn Asp
            20                  25                  30

Pro Ala Tyr Thr Pro Asp Gly Gln Cys Lys Pro Ile Asn Thr Phe Ile
        35                  40                  45

His Ser Thr Thr Gly Pro Val Lys Glu Ile Cys Arg Arg Ala Thr Gly
    50                  55                  60

Arg Val Asn Lys Ser Ser Cys Gln Gln Phe Thr Leu Thr Thr Cys Lys
65                  70                  75                  80

Asn Pro Ile Arg Cys Lys Tyr Ser Gln Ser Asn Thr Thr Asn Phe Ile
                85                  90                  95

Cys Ile Thr Cys Arg Asp Asn Tyr Pro Val His Phe Val Lys Thr Gly
            100                 105                 110

Lys Cys
```

<210> SEQ ID NO 56

-continued

```
<211> LENGTH: 342
<212> TYPE: DNA
<213> ORGANISM: Rana pipiens

<400> SEQUENCE: 56
aaaccgaaag aagaccgtga atgggaaaaa ttcaaaacta acatatcac ttctcagtct    60 gttgctgact tcaactgcaa ccgtactatg aacgacccgg cttacactcc ggacggtcag   120
tgcaaaccga tcaacacttt catccattct actactggtc cggttaaaga aatctgccgt   180
cgtgctactg gtcgtgttaa caaatcttct tgccagcagt tcactctgac tacttgcaaa   240
aacccgatcc gttgcaaata ctctcagtct aacactacta acttcatctg catcacttgc   300
cgtgacaact acccggttca tttcgttaaa actggtaaat gc                     342

<210> SEQ ID NO 57
<211> LENGTH: 39
<212> TYPE: DNA
<213> ORGANISM: Artificial
<220> FEATURE:
<223> OTHER INFORMATION: Artificially synthesized sequence

<400> SEQUENCE: 57
gttaacaaat cttcttgcca gcagttcact ctgactact                          39

<210> SEQ ID NO 58
<211> LENGTH: 39
<212> TYPE: DNA
<213> ORGANISM: Artificial
<220> FEATURE:
<223> OTHER INFORMATION: Artificially synthesized sequence complimentary
      to SEQ ID NO:57

<400> SEQUENCE: 58
cagagtgaac tgctggcaag aagatttgtt aacacgacc                          39

<210> SEQ ID NO 59
<211> LENGTH: 115
<212> TYPE: PRT
<213> ORGANISM: Rana pipiens

<400> SEQUENCE: 59

Met Lys Pro Lys Glu Asp Arg Glu Trp Glu Lys Phe Lys Thr Lys His
 1               5                  10                  15

Ile Thr Ser Gln Ser Val Ala Asp Phe Asn Cys Asn Arg Thr Met Asn
                20                  25                  30

Asp Pro Ala Tyr Thr Pro Asp Gly Gln Cys Lys Pro Ile Asn Thr Phe
            35                  40                  45

Ile His Ser Thr Thr Gly Pro Val Lys Glu Ile Cys Arg Arg Ala Thr
        50                  55                  60

Gly Arg Val Asn Lys Ser Ser Thr Gln Gln Phe Thr Leu Thr Thr Cys
 65                  70                  75                  80

Lys Asn Pro Ile Arg Cys Lys Tyr Ser Gln Ser Asn Thr Thr Asn Phe
                85                  90                  95

Ile Cys Ile Thr Cys Arg Asp Asn Tyr Pro Val His Phe Val Lys Thr
            100                 105                 110

Gly Lys Cys
        115

<210> SEQ ID NO 60
<211> LENGTH: 115
<212> TYPE: PRT
```

<213> ORGANISM: Rana pipiens

<400> SEQUENCE: 60

```
Met Lys Pro Lys Glu Asp Lys Glu Trp Glu Lys Phe Lys Val Lys His
1               5                   10                  15

Ile Thr Ser Gln Ser Val Ala Asp Phe Asn Cys Thr Ser Met Asn
            20                  25                  30

Asn Pro Asp Phe Thr Pro Asp Gly Gln Cys Lys Pro Ile Asn Thr Phe
            35                  40                  45

Ile His Ser Asn Thr Gly Pro Val Lys Glu Ile Cys Arg Arg Ala Ser
        50                  55                  60

Gly Arg Val Asn Lys Ser Ser Thr Gln Gln Phe Pro Leu Thr Thr Cys
65                  70                  75                  80

Lys Asn Pro Lys Arg Cys Lys Tyr Ser Gln Ser Asn Glu Thr Asn Tyr
                85                  90                  95

Ile Cys Ile Thr Cys Arg Asp Asn Tyr Pro Val His Phe Val Lys Ile
            100                 105                 110

Gly Lys Cys
        115
```

<210> SEQ ID NO 61
<211> LENGTH: 115
<212> TYPE: PRT
<213> ORGANISM: Rana pipiens

<400> SEQUENCE: 61

```
Met Lys Pro Lys Glu Asp Lys Glu Trp Val Lys Phe Lys Ala Lys His
1               5                   10                  15

Ile Thr Ser Gln Ser Val Ala Asp Phe Asn Cys Asn Lys Thr Met Asn
            20                  25                  30

Asp Pro Asp Phe Thr Pro Asp Gly Gln Cys Lys Pro Val Asn Thr Phe
            35                  40                  45

Ile His Ser Asn Thr Gly Pro Val Lys Asp Ile Cys Arg Arg Ala Ser
        50                  55                  60

Gly Arg Val Asn Lys Ser Ser Thr Gln Gln Phe Pro Leu Thr Thr Cys
65                  70                  75                  80

Asn Lys Pro Ile Arg Cys Lys Tyr Ser Gln Ser Asn Thr Thr Asn Phe
                85                  90                  95

Ile Cys Ile Thr Cys Arg Asp Asn Tyr Pro Val His Phe Val Lys Ile
            100                 105                 110

Gly Lys Cys
        115
```

<210> SEQ ID NO 62
<211> LENGTH: 2
<212> TYPE: PRT
<213> ORGANISM: Artificial
<220> FEATURE:
<223> OTHER INFORMATION: Artificially synthesized sequence

<400> SEQUENCE: 62

```
Met Ala
1
```

<210> SEQ ID NO 63
<211> LENGTH: 116
<212> TYPE: PRT
<213> ORGANISM: Rana pipiens

```
<400> SEQUENCE: 63

Met Ala Lys Pro Lys Glu Asp Arg Glu Trp Glu Lys Phe Lys Thr Lys
1               5                   10                  15

His Ile Thr Ser Gln Ser Val Ala Asp Phe Asn Cys Asn Arg Thr Met
            20                  25                  30

Asn Asp Pro Ala Tyr Thr Pro Asp Gly Gln Cys Lys Pro Ile Asn Thr
        35                  40                  45

Phe Ile His Ser Thr Thr Gly Pro Val Lys Glu Ile Cys Arg Arg Ala
    50                  55                  60

Thr Gly Arg Val Asn Lys Ser Ser Thr Gln Gln Phe Thr Leu Thr Thr
65                  70                  75                  80

Cys Lys Asn Pro Ile Arg Cys Lys Tyr Ser Gln Ser Asn Thr Thr Asn
                85                  90                  95

Phe Ile Cys Ile Thr Cys Arg Asp Asn Tyr Pro Val His Phe Val Lys
            100                 105                 110

Thr Gly Lys Cys
        115

<210> SEQ ID NO 64
<211> LENGTH: 7
<212> TYPE: PRT
<213> ORGANISM: Artificial
<220> FEATURE:
<223> OTHER INFORMATION: Artificially synthesized sequence

<400> SEQUENCE: 64

Ala Ala Gln Pro Ala Met Ala
1               5

<210> SEQ ID NO 65
<211> LENGTH: 121
<212> TYPE: PRT
<213> ORGANISM: Rana pipiens

<400> SEQUENCE: 65

Ala Ala Gln Pro Ala Met Ala Lys Pro Lys Glu Asp Arg Glu Trp Glu
1               5                   10                  15

Lys Phe Lys Thr Lys His Ile Thr Ser Gln Ser Val Ala Asp Phe Asn
            20                  25                  30

Cys Asn Arg Thr Met Asn Asp Pro Ala Tyr Thr Pro Asp Gly Gln Cys
        35                  40                  45

Lys Pro Ile Asn Thr Phe Ile His Ser Thr Thr Gly Pro Val Lys Glu
    50                  55                  60

Ile Cys Arg Arg Ala Thr Gly Arg Val Asn Lys Ser Ser Thr Gln Gln
65                  70                  75                  80

Phe Thr Leu Thr Thr Cys Lys Asn Pro Ile Arg Cys Lys Tyr Ser Gln
                85                  90                  95

Ser Asn Thr Thr Asn Phe Ile Cys Ile Thr Cys Arg Asp Asn Tyr Pro
            100                 105                 110

Val His Phe Val Lys Thr Gly Lys Cys
        115                 120

<210> SEQ ID NO 66
<211> LENGTH: 22
<212> TYPE: PRT
<213> ORGANISM: Artificial
<220> FEATURE:
<223> OTHER INFORMATION: Artificially synthesized sequence
```

```
<400> SEQUENCE: 66

Met Lys Tyr Leu Leu Pro Thr Ala Ala Gly Leu Leu Leu Ala
1               5                   10                  15

Ala Gln Pro Ala Met Ala
            20

<210> SEQ ID NO 67
<211> LENGTH: 136
<212> TYPE: PRT
<213> ORGANISM: Rana pipiens

<400> SEQUENCE: 67

Met Lys Tyr Leu Leu Pro Thr Ala Ala Gly Leu Leu Leu Ala
1               5                   10                  15

Ala Gln Pro Ala Met Ala Lys Pro Glu Asp Arg Glu Trp Glu Lys
            20                  25                  30

Phe Lys Thr Lys His Ile Thr Ser Gln Ser Val Ala Asp Phe Asn Cys
                35                  40                  45

Asn Arg Thr Met Asn Asp Pro Ala Tyr Thr Pro Asp Gly Gln Cys Lys
50                      55                      60

Pro Ile Asn Thr Phe Ile His Ser Thr Thr Gly Pro Val Lys Glu Ile
65                  70                      75                  80

Cys Arg Arg Ala Thr Gly Arg Val Asn Lys Ser Ser Thr Gln Gln Phe
                85                  90                      95

Thr Leu Thr Thr Cys Lys Asn Pro Ile Arg Cys Lys Tyr Ser Gln Ser
                100                 105                 110

Asn Thr Thr Asn Phe Ile Cys Ile Thr Cys Arg Asp Asn Tyr Pro Val
            115                 120                 125

His Phe Val Lys Thr Gly Lys Cys
        130                 135

<210> SEQ ID NO 68
<211> LENGTH: 115
<212> TYPE: PRT
<213> ORGANISM: Rana pipiens

<400> SEQUENCE: 68

Met Lys Pro Lys Glu Asp Arg Glu Trp Glu Lys Phe Lys Thr Lys His
1               5                   10                  15

Ile Thr Ser Gln Ser Val Ala Asp Phe Asn Cys Asn Arg Thr Met Asn
            20                  25                  30

Asp Pro Ala Tyr Thr Pro Asp Gly Gln Cys Lys Pro Val Asn Thr Phe
        35                  40                  45

Ile His Ser Thr Thr Gly Pro Val Lys Glu Ile Cys Arg Arg Ala Thr
    50                  55                  60

Gly Arg Val Asn Lys Ser Ser Thr Gln Gln Phe Thr Leu Thr Thr Cys
65                  70                  75                  80

Lys Asn Pro Ile Arg Cys Lys Tyr Ser Gln Ser Asn Thr Thr Asn Phe
                85                  90                  95

Ile Cys Ile Thr Cys Arg Asp Asn Tyr Pro Val His Phe Val Lys Thr
            100                 105                 110

Gly Lys Cys
        115

<210> SEQ ID NO 69
<211> LENGTH: 115
<212> TYPE: PRT
```

<213> ORGANISM: Rana pipiens

<400> SEQUENCE: 69

Met Lys Pro Lys Glu Asp Arg Glu Trp Glu Lys Phe Lys Thr Lys His
1               5                   10                  15

Ile Thr Ser Gln Ser Val Ala Asp Phe Asn Cys Asn Arg Thr Met Asn
            20                  25                  30

Asp Pro Ala Tyr Thr Pro Asp Gly Gln Cys Lys Pro Ile Asn Thr Phe
        35                  40                  45

Ile His Ser Thr Thr Gly Pro Val Lys Glu Ile Cys Arg Arg Ala Thr
    50                  55                  60

Gly Arg Val Asn Lys Ser Ser Cys Gln Gln Phe Thr Leu Thr Thr Cys
65                  70                  75                  80

Lys Asn Pro Ile Arg Cys Lys Tyr Ser Gln Ser Asn Thr Thr Asn Phe
                85                  90                  95

Ile Cys Ile Thr Cys Arg Asp Asn Tyr Pro Val His Phe Val Lys Thr
            100                 105                 110

Gly Lys Cys
        115

<210> SEQ ID NO 70
<211> LENGTH: 176
<212> TYPE: PRT
<213> ORGANISM: Rana pipiens

<400> SEQUENCE: 70

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
            35                  40                  45

Trp Trp Glu Leu Arg Gly Gly Ser Gly Gly Pro Gly Gly Ser Lys Pro
    50                  55                  60

Lys Glu Asp Arg Glu Trp Glu Lys Phe Lys Thr Lys His Ile Thr Ser
65                  70                  75                  80

Gln Ser Val Ala Asp Phe Asn Cys Asn Arg Thr Met Asn Asp Pro Ala
                85                  90                  95

Tyr Thr Pro Asp Gly Gln Cys Lys Pro Ile Asn Thr Phe Ile His Ser
            100                 105                 110

Thr Thr Gly Pro Val Lys Glu Ile Cys Arg Arg Ala Thr Gly Arg Val
        115                 120                 125

Asn Lys Ser Ser Cys Gln Gln Phe Thr Leu Thr Thr Cys Lys Asn Pro
    130                 135                 140

Ile Arg Cys Lys Tyr Ser Gln Ser Asn Thr Thr Asn Phe Ile Cys Ile
145                 150                 155                 160

Thr Cys Arg Asp Asn Tyr Pro Val His Phe Val Lys Thr Gly Lys Cys
                165                 170                 175

<210> SEQ ID NO 71
<211> LENGTH: 528
<212> TYPE: DNA
<213> ORGANISM: Rana pipiens

<400> SEQUENCE: 71
aactctgact ctgaatgccc gctgtctcat gacggttact gcctgcatga cggtgtttgc    60

```
                                                  -continued
atgtacatcg aagctctgga caaatacgct tgcaactgcg ttgttggtta catcggtgaa      120
cgttgccagt accgtgacct gaaatggtgg gaactgcgtg gtggttctgg tggtccgggt      180
ggttctaaac cgaaagaaga ccgtgaatgg gaaaaattca aaactaaaca tatcacttct      240
cagtctgttg ctgacttcaa ctgcaaccgt actatgaacg acccggctta cactccggac      300
ggtcagtgca aaccgatcaa cactttcatc cattctacta ctggtccggt taaagaaatc      360
tgccgtcgtg ctactggtcg tgttaacaaa tcttcttgcc agcagttcac tctgactact      420
tgcaaaaacc cgatccgttt caaatactct cagtctaaca ctactaactt catctgcatc      480
acttgccgtg acaactaccc ggttcatttc gttaaaactg gtaaatgc                  528

<210> SEQ ID NO 72
<211> LENGTH: 55
<212> TYPE: DNA
<213> ORGANISM: Artificial
<220> FEATURE:
<223> OTHER INFORMATION: Artificially synthesized sequence

<400> SEQUENCE: 72
ccaactctga ctctgaatgc ccgctgtctc atgacggtta ctgcctgcat gacgg          55

<210> SEQ ID NO 73
<211> LENGTH: 54
<212> TYPE: DNA
<213> ORGANISM: Artificial
<220> FEATURE:
<223> OTHER INFORMATION: Artificially synthesized sequence

<400> SEQUENCE: 73
ggtggttctg gtggtccggg tggttctaaa ccgaaagaag accgtgaatg ggaa            54

<210> SEQ ID NO 74
<211> LENGTH: 54
<212> TYPE: DNA
<213> ORGANISM: Artificial
<220> FEATURE:
<223> OTHER INFORMATION: Artificially synthesized sequence

<400> SEQUENCE: 74
agaaccaccc ggaccaccag aaccaccacg cagttcccac catttcaggt cacg            54
```